United States Patent
Ozaki

(10) Patent No.: US 9,974,648 B2
(45) Date of Patent: May 22, 2018

(54) TEMPLATE FOR FORMING VALVE LEAFLET

(71) Applicants: TOHO UNIVERSITY, Tokyo (JP); JAPANESE ORGANIZATION FOR MEDICAL DEVICE DEVELOPMENT, INC., Tokyo (JP)

(72) Inventor: Shigeyuki Ozaki, Tokyo (JP)

(73) Assignees: TOHO UNIVERSITY, Tokyo (JP); JAPANESE ORGANIZATION FOR MEDICAL DEVICE DEVELOPMENT, INC., Tokyo (JP)

( * ) Notice: Subject to any disclaimer, the term of this patent is extended or adjusted under 35 U.S.C. 154(b) by 112 days.

(21) Appl. No.: 15/127,416

(22) PCT Filed: Mar. 19, 2015

(86) PCT No.: PCT/JP2015/058338
§ 371 (c)(1),
(2) Date: Sep. 20, 2016

(87) PCT Pub. No.: WO2015/141798
PCT Pub. Date: Sep. 24, 2015

(65) Prior Publication Data
US 2017/0189173 A1     Jul. 6, 2017

(30) Foreign Application Priority Data
Mar. 20, 2014 (JP) .................. 2014-058056

(51) Int. Cl.
*G01B 3/14* (2006.01)
*A61F 2/24* (2006.01)

(52) U.S. Cl.
CPC .... *A61F 2/2415* (2013.01); *A61F 2220/0075* (2013.01); *A61F 2240/005* (2013.01)

(58) Field of Classification Search
CPC ...................................... A61F 2/2415
(Continued)

(56) References Cited

U.S. PATENT DOCUMENTS 2,322,028 A * 6/1943 Johnson .................. C03B 33/04
294/189
2,323,145 A * 6/1943 Mabry .................. A45D 29/004
132/285
(Continued)

FOREIGN PATENT DOCUMENTS

JP    2009-077838 A    4/2009
JP    3175944 U        6/2012
JP    5106019 B2       12/2012

OTHER PUBLICATIONS

International Search Report of International Application No. PCT/JP2015/058338 completed May 7, 2015 and dated May 19, 2015 (3 pages).
(Continued)

Primary Examiner — G. Bradley Bennett
(74) Attorney, Agent, or Firm — Pyprus Pte Ltd

(57) ABSTRACT

A template 13 comprises a cusp base forming part 11 having a shape corresponding to a cusp base is provided to obtain cusp material for dispersing stresses exerted on the cusp. Such a cusp forming template may further comprise wing forming parts 15 corresponding to wing parts provided outside the cusp base forming part 11. As examples of the wing forming part, there may be employed a single or plural holes provided at a part or parts corresponding to the outline of each wing, and guide parts provided at parts corresponding to the outline of wings.

6 Claims, 4 Drawing Sheets

(58) Field of Classification Search
USPC .................................................. 33/563–566
See application file for complete search history.

(56) References Cited

U.S. PATENT DOCUMENTS

| | | | |
|---|---|---|---|
| 4,688,330 A * | 8/1987 | Konrad | B43L 13/205 33/27.03 |
| 7,156,017 B1 * | 1/2007 | Ingraselino | B41M 1/12 101/115 |
| 2004/0148018 A1 | 7/2004 | Carpentier et al. | |
| 2006/0229716 A1 * | 10/2006 | Mitrev | A61B 5/1072 623/2.11 |
| 2008/0052940 A1 * | 3/2008 | Manley | D04B 31/00 33/563 |
| 2010/0011564 A1 * | 1/2010 | Millwee | A61F 2/2415 29/527.3 |
| 2010/0018447 A1 | 1/2010 | Holecek | |
| 2011/0251598 A1 | 10/2011 | Ozaki | |
| 2011/0313515 A1 | 12/2011 | Quadri et al. | |
| 2012/0204437 A1 * | 8/2012 | Nethery | B43L 7/005 33/566 |
| 2018/0036121 A1 * | 2/2018 | Li | A61F 2/2415 |

OTHER PUBLICATIONS

Office Action of Canadian patent application No. 2,942,647 dated Jul. 13, 2017 (4 pages).

* cited by examiner

Fig. 3
Fig.3A
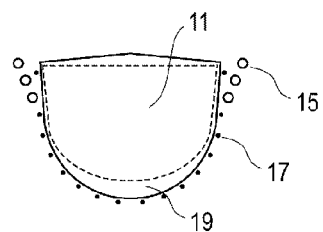
Fig.3B
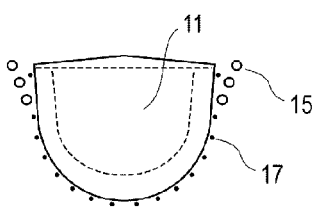
Fig.3C
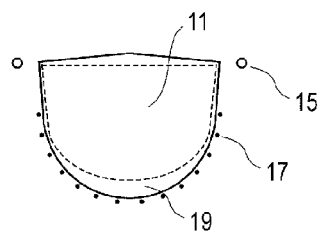
Fig.3D
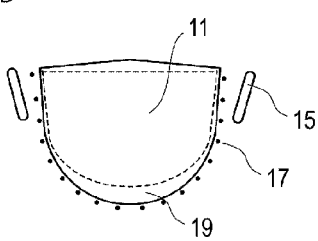
Fig. 4
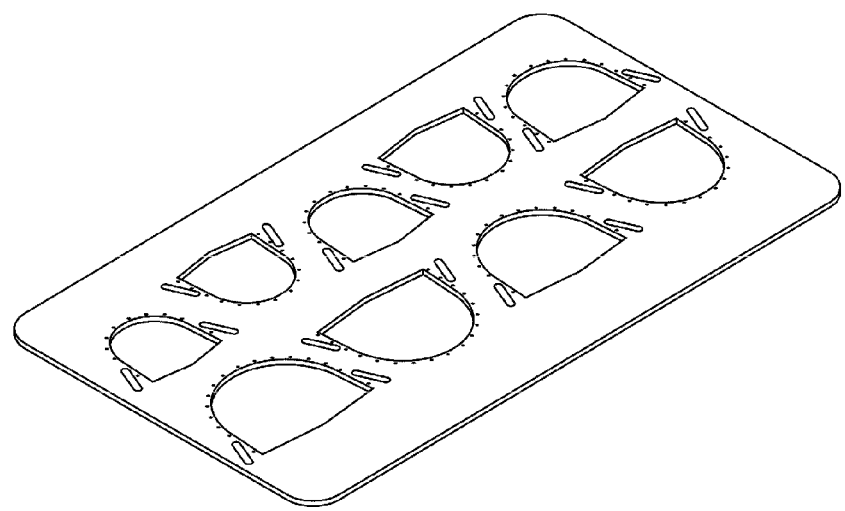

TEMPLATE FOR FORMING VALVE LEAFLET

TECHNICAL FIELD

The present invention relates to a cusp forming template used, in implementing, e.g. treatment of aortic valvuloplasty, and/or aortic valve reconstruction, used for forming cusp materials from artificial membrane or bio-membrane.

BACKGROUND ART

In the Japanese Patent No. 5106019 publication (which will be referred to as the Patent document 1 described below), there is disclosed a cusp forming template. The template in this document includes or contains: a substantially semicircular cusp base forming part having, as a diameter, a sum of a nominal diameter (a diameter of a cylinder which forms an arcuate surface of a sizer block of which size is in agreement with both commissure parts of cut cusps) and a seam allowance; and a line drawing part comprising a coaptation zone forming part continuous to the cusp base forming part. Such a template is used to draw lines on a membrane to cut the membrane along those lines. Thus, cusp forming materials for cusp formation can be provided.

CITATION LIST

Patent Document

[Patent document 1] Japanese Patent No. 5106019 Publication

SUMMARY OF INVENTION

Technical Problem

The template of the above-described Patent document 1 can provide cusp materials having a size including both the size of the cusp and the seam allowance. It is desirable to disperse stresses exerted on the cusp thus to form more resistant cusps. For this reason, a template for obtaining such cusp materials is desired.

Solution to Problem

The present invention is concerned with a cusp forming template. This cusp forming template is such that cusp forming parts are formed thereafter to provide wing forming parts for drawing wings. In order to cut cusp materials from a membrane, the membrane is cut with lines (or dots) drawn by the wing forming part being as an indication thus to have ability to form cusp materials. In addition, e.g., in implementing treatment of aortic valvuloplasty, the shape of a cusp drawn by the cusp forming part will be useful in preparing such cusp.

The present invention is concerned with a cusp forming template. Such cusp forming template is used for, e.g., aortic valvuloplasty and/or aortic valve reconstruction. Further, such a template contains a cusp base forming part 11 having a shape corresponding to the cusp base. This cusp forming template further contains wing forming parts 15 corresponding to respective wing parts provided outside the cusp base forming part 11.

An example of the wing forming part may be a single or plural holes provided at a part or parts corresponding to the outline of the wing. Moreover, another example of the wing forming part may be a guide part provided at a part corresponding to the outline of the wing. It is preferable that each wing forming part is provided, e.g., at a part of more than 40% to less than 80% of the side surface of the cusp base forming part 11 from the side surface upper end of the cusp base forming part 11.

It is preferable that scales indicating portions sewed in implementing treatment are provided at respective cusp base forming parts 11. Such scales may be equidistantly provided, or may be caused to correspond to portions sewed in practice.

Advantageous Effect

When any cusp materials are provided on the basis of the template of the present invention, wing parts are formed on the side surfaces of the cusp forming part. For example, such wing parts are folded back to sew them with artery to thereby have ability to disperse stresses exerted on the seawing part so that the cusp is permitted to have resistance.

BRIEF DESCRIPTION OF DRAWINGS

FIG. 3 is a diagram illustrating respective examples of cusp base forming parts and wing forming parts.

FIG. 4 is a reference perspective diagram of a template having cusp base forming parts and wing forming parts which are illustrated in FIG. 3D.

DESCRIPTION OF EMBODIMENT

Preferred exemplary embodiments for carrying out the present invention will now be described with reference to the attached drawings. It should be noted that the present invention is not limited to exemplary embodiments described below, but may also include an exemplary embodiment or embodiments that those persons skilled in the art modify or change as occasion demands from the following exemplary embodiments within the scope which is self-explanatory therefor.

Figure 1:
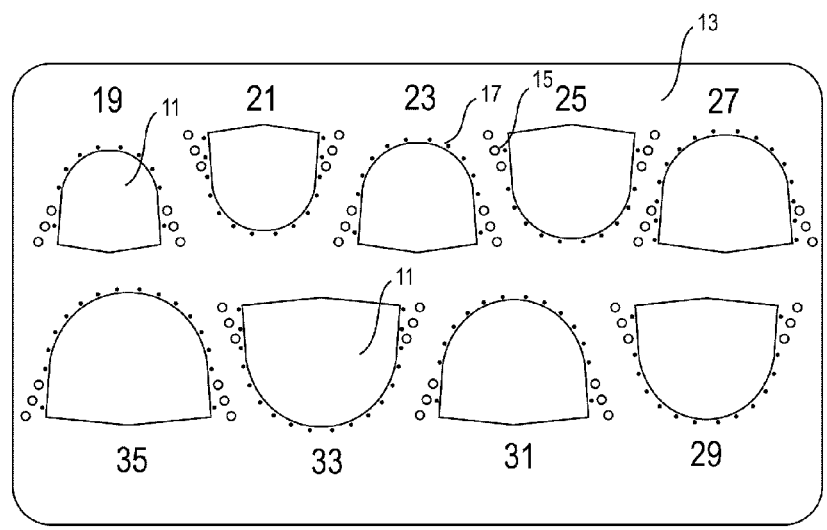
FIG. 1 is a diagram illustrating an example of a cusp forming template.
Figure 2:
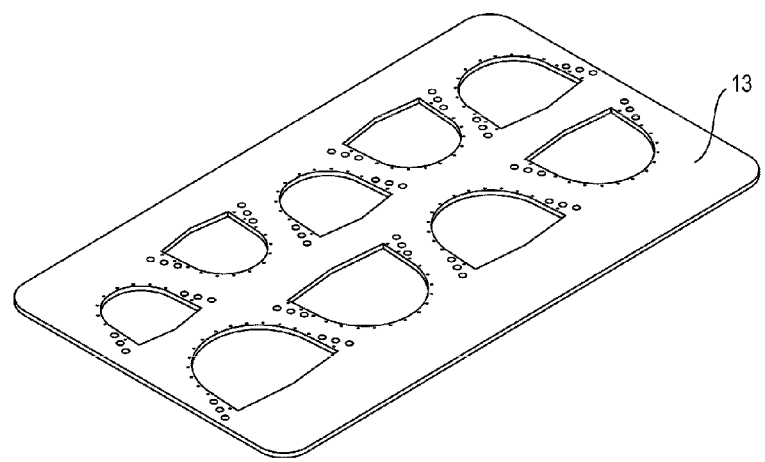
FIG. 2 is a reference perspective diagram of the template of FIG. 1.

The present invention relates to a cusp forming template. FIG. 1 is a diagram illustrating an example of a cusp forming template. FIG. 2 is a reference perspective diagram of the template of FIG. 1. Each cusp forming template is a template used for, e.g., aortic valvuloplusty. Further, as illustrated in FIG. 1, this template 13 contains cusp base forming parts 11 each having a shape corresponding to the cusp base. This cusp forming template further contains wing forming parts 15 corresponding to respective wing parts provided outside the cusp base forming parts 11. Numbers in FIG. 1 are numbers assigned also to corresponding sizers.

FIG. 3 is a diagram illustrating examples of the cusp base forming parts and the wing forming parts. As illustrated in FIG. 3A, there is illustrated an example where a lateral upper end part of each cusp base forming part 11 exists at a position corresponding to a commissure part. As in this figure, the portion encompassed by the edge of the cusp base forming part 11 and dotted lines is a seam allowance. These dotted lines indicate the shape of the cusp. In this case, such a seam allowance 19 is provided within a region including a lower end part of the cusp base forming part 11. At both side surfaces of the cusp base forming part 11, there are provided a plurality of holes each serving as the wing forming part 15.

The upper part of the cusp base forming part 11 may have a rectangular similarly to the above-mentioned Japanese Patent No. 5106019 publication, or may have an inverse-trapezoidal shape. Moreover, slanting slopes may be also provided toward the upper center in addition to the rectangular shape or the inverse-trapezoidal shape. These upper portions are parts constituting a coaptation zone referred to as in the previously mentioned Japanese Patent No. 5106019 publication.

As the cusp base forming part 11, there may be used a cusp base forming part which has a shape similar to that of the previously mentioned Japanese Patent No. 5106019 publication. FIG. 3B indicates an example of a template having a size of a sum of the size of the seam allowance and the size of the cusp. In this case, the cusp base formed by the cusp base forming part 11 may have a shape in consideration of the seam allowance in addition to the size of an actual cusp.

The wing forming parts 15 may each comprise a single hole as illustrated in FIG. 3C. Because this hole exists, a membrane is cut off with such a hole being as an indication, thereby making it possible to form a wing having a size suitable in treatment.

The wing forming parts 15 may each have a groove shape as illustrated in FIG. 3D. When a writing tool is moved along such grooves, it becomes possible to draw lines serving as indication at the membrane in cutting such membrane along the wing parts. FIG. 4 is a reference perspective diagram of the template including the cusp base forming parts and the wing forming parts which are illustrated in FIG. 3D.

Figure 5:
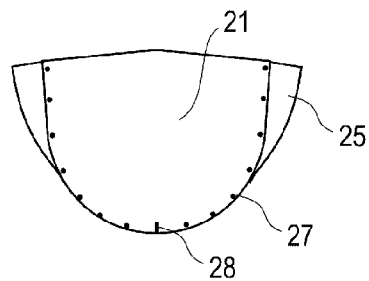
FIG. 5 is a diagram illustrating an example of a cusp material which is cut out using the template.

FIG. 5 is a diagram illustrating an example of a cusp material which is cut out by using the template. As illustrated in FIG. 5, this cusp material contains a cusp base 21, and wing parts 25. Further, scales 27 are drawn on the cusp base 21, and an index 28 is drawn at the lower end of the cusp base 21.

The wing part 25 is a part to be fixed to the artery, etc. in the state folded in performing treatment and overlap with the cusp base 21. When such a situation is taken into consideration, it is said that the wing part serves as a part which provides a seam allowance. The wing part is a portion to be bent back. For this reason, it is preferable that the wing forming part does not exist over the entirety of circumference except for the upper surface of the cusp base forming part 11 as in the case of the seam allowance of the Japanese Patent No. 5106019 publication, but may be provided at, e.g., a part at more than 40% to less than 80% (or more than 50% to less than 70%) of the side surface upper end of the cusp base forming part 11. This range is a range when a vertical line is fallen down from the middle point of a line connecting side surface upper ends of the two cusp base forming parts 11, and a distance down to the lower end of the cusp base forming part 11 is assumed to be 100%.

An example of the wing forming part may be a single hole or plural holes provided at a portion (or the entirety) of a part corresponding to the outline of the wing part. Moreover, another example of the wing forming part is a guide part provided at a part corresponding to the outline of the wing. The guide part is a groove for drawing, e.g., lines corresponding to wings. Such a groove may be used to thereby permit dots or lines serving as indication of the wing part to be drawn.

It is preferable that there may be provided scales 27 indicating portions sewed in implementing treatment of operation for forming a valve like the aortic valvuloplasty or the aortic valve reconstruction at edge portions of the cusp base forming part 11. Such scales may be equidistantly provided, or may be provided in correspondence with portions actually sewed. Such scales may be provided at, e.g., edge portions of the cusp base forming part 11. The aortic valve reconstruction serves to entirely replace three valve lines into new cusps, and the aortic valvuloplasty serves to cause at least one of original valve lines to be left thereafter to replace the remaining one or ones into new cusp or cusps.

An example of the aortic valve reconstruction for forming aortic valve using cusp materials formed by own pericardiums of a patient will now be described. In this case, after sternum is exposed, median sternotomy is implemented. Thereafter, such pericardiums are cut. The extracorporeal circulation based on artificial cardiopulmonary is performed in the state where the heart is exposed to stop the heart rate thereafter to cause aortic valve or valves to be exposed. On the other hand, the pericardiums acquired in advance are expanded by means of thread to immerse them into a tissue fixation solution (e.g., solution containing glutaraldehyde) in the state fixed thereto.

Next, any one of three cusps of the aortic valves is or are removed. A cusp sizer is caused to be successively in contact with part or parts which have been cut to measure size or sizes (based on distances between commissure parts) of the cut cusps. The pericardium or pericardiums is or are taken out from the tissure fixation solution. Further, lines are drawn on the pericardium or pericardiums along the cusp base forming part 11 of the template which corresponds to the cusp sizer (a sizer having a size corresponding to the commissure part of the cut cusp or cusps). More specifically, since the cusp base forming part 11 is adapted to be hollow therewithin, a writing tool is caused to trace along the edge of the cusp base forming part 11, thereby making it possible to draw lines for cusp base on the pericardium or pericardiums. Since it is sufficient that lines for cusp base drawn on the pericardium or pericardiums serve as an indication in performing treatment, continuous lines may be employed, or lines or dots indicating the principal outer shape of valve line may be employed. Thereafter, each wing forming part 15 is used to draw corresponding marks on the wing forming part. The shape of the mark corresponding to the wing forming part may be various depending upon the kind of the template. An example of the mark corresponding to the wing forming part may be lines, or dot or dots at a single or plural portions as described above. When there is used a template provided with scales on the cusp base forming part 11, marks indicating portions sewed in implementing treatment to the pericardium may be drawn as occasion demands with respective scales being as an indication.

Next, each pericardium is cut with marks corresponding to the wing forming part being as an indication to provide cusp materials. Such cusp materials may be immersed into, e.g., saline.

Figure 6:
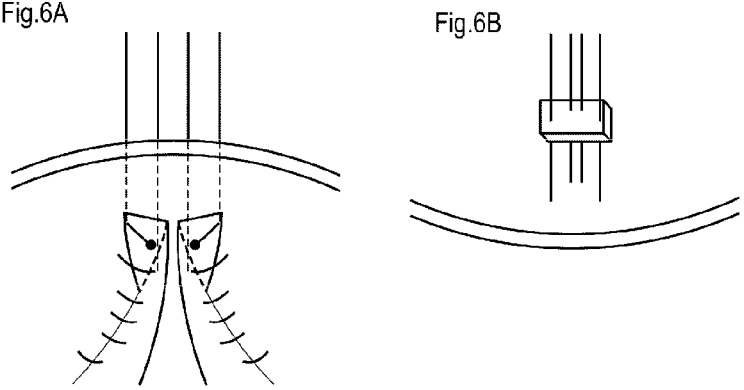
FIG. 6 is a conceptual diagram illustrating the state where the cusp material is sewed with a blood vessel.

FIG. 6 is a conceptual diagram indicating the state where the cusp materials are sewed with blood vessel such as aorta. As illustrated in FIG. 6A, the wing parts 25 of the cusp material are bent so that the wing parts 25 are located on the inside (i.e., are bent in a mountain form). The fundamental work for a more practical treatment method is similar to that in the Japanese Patent No. 5106019 publication. Namely, the index 28 formed at a position corresponding to the central point of the cusp is caused to be summit to set or put thread at a position that the index 28 points out to sew the central point of the cusp base 25. Sewing is advanced toward the commissure part with the central point being as a reference. It is preferable that spacing between needles is narrowed within the lower end region of the cusp base 25. More specifically, it is preferable that the pitch of the needle is caused to be ⅓ (one third) as compared to the side surface region of the cusp base 25 within the lower end region of the cusp base 25.

When sewing is advanced until a portion in the vicinity of the commissure part, the scale part of the uppermost part is left to project the needle toward the outside of blood vessel. Further, sewing of adjacent cusp base is similarly advanced to allow the scale part of the uppermost part to be left to project the needle toward the outside of the blood vessel. A thread different from that used at a tip to which needles are attached at the both ends is penetrated from the outside of the blood vessel toward the inside of the blood vessel through the scale portion of the uppermost part at the wing part of one cusp material. When explanation will be given in more practical sense, the thread is passed from the point A toward the point B. Further, the thread from the point B is passed through the point D, and is then protruded toward the felt side. On the other hand, the needle in the vicinity of the point A is also passed through the point C, and is then protruded toward the felt side. Thus, there results the state where four needles are directed toward the outside of the blood vessel (FIG. 6A). A single felt is penetrated by means of these four needles (FIG. 6B). These four needles are: a needle sewed up from the lower end of a certain cusp material; a needle sewed up from the lower end of a cusp material adjacent to the certain cusp material; and two needles provided on both sides of the thread existing on the uppermost part. Further, the thread is connected in the state penetrated through the felt (FIG. 6C). In this way, it is possible to fix the cusp materials to the blood vessel. The above-described example is directed to the example where medical thread is used to fix the cusp material to the blood vessel. However, cusp material may be fixed to the blood vessel using means except for the thread, such as, for example, medical stapler.

Figure 7:
FIG. 7 is a photograph substituted with a drawing indicating artery in which new cusps were formed in implementing treatment of aortic valve reconstruction using the template of the present invention.

FIG. 7 is a photograph substituted with a drawing indicating artery in which new cusps were formed in implementing treatment of aortic valve reconstruction using the template of the present invention.

INDUSTRIAL APPLICABILITY

The present invention can be suitably utilized in the field of the medical equipment.

REFERENCE SIGNS LIST

11 . . . Cusp base forming part, 13 . . . Template, 15 . . . Wing forming part, 17 . . . Scale

The invention claimed is:

1. A template (13) which comprises a cusp base forming part (11) having a shape corresponding to a cusp base, further comprising:
   a wing forming part (15) which corresponds to a wing part provided outside the cusp base forming part (11).

2. The template according to claim 1,
   wherein the wing forming part comprises a single or plural holes provided at a part or parts corresponding to the outline of a wing or wings.

3. The template according to claim 1,
   wherein the wing forming part comprises a guide part provided at a part corresponding to the outline of a wing.

4. The template according to claim 1,
   wherein the wing forming part is provided at a part of more than 40% to less than 80% of the side surface of the cusp base forming part (11) from a side surface end of the cusp forming base part (11).

5. The template according to claim 1,
   wherein the cusp base forming part (11) is provided with a scale (17) indicating a portion sewed in implementation of treatment.

6. The template according to claim 1,
   wherein the cusp base forming part (11) is provided with equidistant scales (17).

* * * * *